US006479251B1

(12) United States Patent
Singh (10) Patent No.: US 6,479,251 B1
(45) Date of Patent: Nov. 12, 2002

(54) COLORIMETRIC TEST FOR AGENTS THAT INDUCE MITOCHONDRIAL DYSFUNCTION

(75) Inventor: Keshav K. Singh, Ruxton, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/668,365

(22) Filed: Sep. 25, 2000

Related U.S. Application Data (60) Provisional application No. 60/155,872, filed on Sep. 24, 1999.

(51) Int. Cl.[7] .............................. C12Q 1/02; C12Q 1/04; C12Q 1/06
(52) U.S. Cl. .............................. 435/29; 435/34; 435/39
(58) Field of Search ............................... 435/29, 34, 39

(56) References Cited

U.S. PATENT DOCUMENTS

| 5,352,581 A | 10/1994 | Resnick et al. ................. 435/6 |
| 5,798,240 A | * 8/1998 | Martinis et al. |

FOREIGN PATENT DOCUMENTS

| EP | 0 512 830 A2 | 11/1992 |
| WO | WO 99/53024 | 10/1999 |
| WO | WO 00/47761 | 8/2000 |

OTHER PUBLICATIONS

International Search Report, Appl. No. PCT/US00/26295, Apr. 6, 2001, pp. 1–3.
Toma et al., "The Recombinogenic And Mutagenic Influence Of Formaldehyde On Yeast", Proceedings of The Latvian Academy of Sciences, Sec. B., No. 3, vol. 50, 1996, pp. 126–129.
J. Daniel, "Measuring The Toxic Effects Of High Gene Dosage On Yeast Cells", Mol. Gen. Genet, No. 3, vol. 253, 1996, pp. 393–396.
Philip S. Perlman and Henry R. Mahler, "Methods in Enzymology" ISBN 0–12–182155–2 Academic Press, Inc. 19983 v. 97 pp. 374–395.
Bryan A. Jones and Walton L. Fangman, "Genes and Development" ISSN 0890–9369 Cold Spring Harbour Laboratory Press 1992 v.6 pp. 380–389.
Lene Juel Rasmussen and Keshav K. Singh, "Mitochondrial DNA Mutations in Aging, Disease and Cancer" Ch. 6, pp. 114–126, 1998 Springer–Verlag and R.G. Landes Company.
Kylie F. Keshav and Shonen Yoshida, "Mitochondrial DNA Mutations in Aging, Disease and Cancer" Ch. 5, pp. 101–113, 1998 Springer–Verlag and R.G. Landes Company.
Alfred S. Lewin, "Mitochondrial DNA Mutations in Aging, Disease and Cancer" Ch. 2, pp. 17–41, 1998 Springer–Verlag and R.G. Landes Company.
Sharon Hesterlee, "Mitochondrial Myopathy: An Energy Crisis in the Cells", Quest v.6, No. 4, Part I, p–1–5 and Part II pp. 1–5, Aug. 1999.
Dongchon Kang, Koichiro Takeshige, Mutsuo Sekiguchi and Keshav K. Singh, "Mitochondrial DNA Mutations in Aging, Disease and Cancer", Ch. 1. pp. 1–15, 1998 Springer–Verlag and R.G. Landes Company.
Keshav K Singh, James Russell, Barbara Sigala, Yonggong Zhang, Jerry Williams and Kylie F. Keshav, "Mitochondrial DNA Determines the Cellular Response to Cancer Therapeutic Agents", Oncogene (1999) v. 18, pp. 6641–6646.
S.E. Reaume and E.L. Tatum, "Analytical Biochemistry", ISSN 003–2697 New York, Academic Press 1949 v. 22 pp. 0331–338.

* cited by examiner

Primary Examiner—Ralph Gitomer
Assistant Examiner—Mahreen Chaudhry
(74) Attorney, Agent, or Firm—Banner & Witcoff, Ltd.

(57) ABSTRACT

Test agents are screened for their effects on mitochondria using a bioassay. Mutant cells with mutations in their mitochondria are readily detectable. Agents which induce such mutations are thereby identified as potential disease causing agents.

22 Claims, 6 Drawing Sheets

100 × MAG.

FIG. 4A

GROWTH COMPARISON OF HAPLOID YEAST CELLS

FIG. 4B

GROWTH COMPARISON OF DIPLOID YEAST CELLS

FIG. 6A Wild type

FIG. 6B rho⁰

FIG. 6C Adriamycin

FIG. 6D Hydrogen peroxide

FIG. 6E UV

FIG. 6F MMS

COLORIMETRIC TEST FOR AGENTS THAT INDUCE MITOCHONDRIAL DYSFUNCTION

This application claims the benefit of provisional application U.S. Ser. No. 60/155,872 filed Sep. 24, 1999, the disclosure of which is expressly incorporated herein.

TECHNICAL FIELD OF THE INVENTION

This invention is related to the area of toxicology, mutagenesis, and carcinogenesis testing.

BACKGROUND OF THE INVENTION

Mitochondria are the major sites of energy (ATP) production in the cell. Mitochondria also perform many other cellular functions. These include respiration, heme, lipid, amino acid and nucleotide biosynthesis. Mitochondria also maintain the intracellular homeostasis of inorganic ions and initiate programmed cell death (1–5). Mitochondria contain approximately 1000 proteins. However, only 13 of these proteins are encoded by human mitochondrial DNA (mitDNA). These 13 proteins constitute the essential subunits of the electron transport system (1–5). All other mitochondrial proteins are synthesized in the cytoplasm and transported into mitochondria. Proteins destined for mitochondria contain a mitochondrial transport signal (MTS, 5).

Mitochondria are the major source of endogenous reactive oxygen species (ROS) in cells because they contain the electron transport chain that reduces oxygen to water by addition of electrons during oxidative phosphorylation. Mitochondrial respiration accounts for about 90% of cellular oxygen consumption (1–5). Therefore, each mitochondrion produces $10^7$ ROS molecules/cell/day during normal oxidative phosphorylation (6–7). Human mitDNA, unlike nuclear DNA, contains no introns and has no protective histones proteins. These features of mitDNA make it more vulnerable than nuclear DNA to damage by ROS produced within the mitochondria (and by environmental agents such as ionizing radiation which produce ROS). Consistent with this finding mitDNA appears to mutate at a rate ten times higher than nuclear DNA (8). Mutations in mitDNA are involved in the pathogenesis of a variety of diseases including cancer (1, 9–10), heart disease (11), cardiomyopathies, diabetes, degenerative diseases such as Parkinson's, Alzheimer's, Huntington's disease, and other neurological disorders (1,12). Accumulation of somatic mutations of mitDNA also appears to be a constant feature of normal aging in all vertebrates thus far examined (1). The genetic changes observed in these diseases range from point mutations to deletions or insertions in the mitDNA(13–15).

There is a continuing need in the art for improved means of testing agents which may be harmful to the health of humans as well as a need for identification of agents for treating important human diseases in which mitochondrial dysfunction has been implicated.

SUMMARY OF THE INVENTION

It is an object of the present invention to provide a method for identifying agents which induce mitochondrial dysfunction.

It is another object of the present invention to provide a method for identifying agents which enhance mitochondrial function.

It is still another object of the invention to provide a kit for testing mitochondrial function.

These and other objects of the invention are achieved by providing one or more of the following embodiments. In one embodiment, a method is provided for identifying agents which induce mitochondrial dysfunction. Eukaryotic cells which are auxotrophic for adenine are contacted with a test agent. The eukaryotic cells are cultured on a medium comprising glucose. The fraction of the eukaryotic cells which appear white is scored. The white eukaryotic cells are tested to determine the ability to grow on a non-fermentable carbon source. The test agent is identified as a mitochondrial dysfunction inducer if the test agent increases the fraction of the eukaryotic cells (a) which become white and (b) which are unable to grow on the non-fermentable carbon source, relative to control eukaryotic cells which have not been contacted with the test agent.

According to another embodiment of the invention, a method is provided for identifying agents which enhance mitochondrial function. Eukaryotic cells which are auxotrophic for adenine and defective in mitochondrial function are contacted with a test agent. The eukaryotic cells are cultured on a medium comprising glucose. The fraction of the eukaryotic cells which appear red is scored. The red eukaryotic cells are tested to determine the ability to grow on a non-fermentable carbon source. The test agent is identified as a mitochondrial function enhancer if the test agent increases the fraction of the eukaryotic cells (a) which become red and (b) which are able to grow on the non-fermentable carbon source, relative to control eukaryotic cells which have not been contacted with the test agent.

According to still another embodiment of the invention, a kit is provided. The kit comprises a sample of eukaryotic cells which are auxotrophic for adenine; a non-fermentable medium for growth of the eukaryotic cells; a fermentable medium for cell growth of the eukaryotic cells; and instructions for testing agents for the ability to affect mitochondrial function.

The present invention thus provides the art with a simple bioassay system which can be used by toxicologists to determine the potential genetic and non-genetic hazard to mitochondria of a variety of suspected or known mutagens, toxins, or carcinogens.

BRIEF DESCRIPTION OF THE DRAWINGS

FIGS. 1A and 1B show visual color identification of mitochondrial dysfunction. The wild type *S. cerevisiae* YPH499 was gown in YPD (1% yeast extract, 2% bactopeptone and 2% dextrose) to log phase at 30° C. The log phase culture was centrifuged, resuspended in water containing adriamycin (150 µg/ml) for one hour. Appropriate dilutions of the culture were plated on YPD agar and incubated at 30° C. for 3–4 days. FIG. 1A: plate on the left shows untreated control cells, plate on the right shows adriamycin treated cells. FIG. 1B: white colonies from treated cells in FIG. 1A wee replicated on to agar medium containing 2% dextrose (left) and 2% glycerol (right).

FIG. 2 shows the percent increase in white colonies containing dysfunctional mitochondria. The wild type *S. cerevisiae* YPH499 was grown in YPD to log phase at 30° C. The culture was centrifuged, resuspended in water containing various concentrations of adriamycin as indicated for one hour. Appropriate dilutions of the culture were plated on YPD agar and incubated at 30° C. Colonies were counted after 3–4 days. Values presented are the average of four determinants.

FIGS. 3A–3D show mitochondrial genome changes induced by adriamycin. Various white *S. cerevisiae* colonies produced after treatment with adriamycin were grown to log phase and stained with DAPI, which stains DNA. FIG. 3A:

wild type; FIG. 3B: a Rho⁰ strain (devoid of mitochondrial genome); FIG. 3C: a representative white cell lacking mitochondrial genome; and FIG. 3D: a representative cell containing mutant mitochondrial DNA.

FIG. 4A: Various white colonies produced after treatment with adriamycin were streaked on YP glycerol plates. FIG. 4B: The same white colonies were mated with an opposite mating type strain of yeast lacking mitochondrial DNA on YPD plates. The diploid yeast strains were tested for growth on YP glycerol medium.

FIG. 6A: Wild type; FIG. 6B: A Rho⁰ strain; FIG. 6C: adriamycin; FIG. 6D: hydrogen peroxide; FIG. 6E: UV; FIG. 6F: Methylmethane sulfonate. For FIGS. 6C–F, the cells on the right contains mutant mitDNA and the cell on the left lacks a mitochondrial genome. Far right column shows growth on YPD.

DETAILED DESCRIPTION

It is a discovery of the present invention that changes in the mitochondrial genome can be readily detected using a simple set of screening steps. Thus agents, whether chemical or physical, can be readily tested for their effects on mitochondrial genomes. As validation of the principle of the invention, the chemotherapeutic agent adriamycin has been tested in the assay system and has been found to induce mutations in the mitochondrial genome.

The bioassay of the invention can be used in a forward or a backward direction, i.e., to either find agents which induce mutations in mitochondrial genomes or which suppress the phenotype of such mutations. Any eukaryotic cells can be used in the bioassay system, although yeast cells are preferred. Adenine auxotrophs are used because they accumulate a red pigment which can be detected visually. Alternatively an optical sensing machine can be used to distinguish between red and white colonies. The red pigment accumulation typically occurs under culture conditions which employ glucose (dextrose). When such adenine auxotrophs are grown on glucose most cells appear red, but rare cells will be observed that appear white. Contacting the cells with a test agent prior to the culturing on glucose may increase the ratio of the population of cells which appear white. An agent which increases the ratio is a candidate mitochondrial DNA damaging agent. To confirm that the agent is damaging the mitochondrial DNA, the detected white cells can be tested for the ability to grow on a non-fermentable carbon source, such as glycerol, succinate, acetate, pyruvate, fumarate, or lactate. Cells with damaged mitochondrial DNA will not grow on such carbon sources.

In one embodiment of the invention the cells used are yeast cells. The yeast cells can be of any genus and species, but Saccharomyces cerevisiae are preferred due to the extensive genetic knowledge accumulated in the art about this species. The adenine mutation can be in any gene of the adenine pathway which causes the cell to accumulate red pigment. Suitable genes include ade1 and ade2.

When performing the bioassay in the reverse direction to identify agents which enhance mitochondrial function, one begins with cells which are both adenine auxotrophic and mitochondrial function deficient. Cells are then assayed to detect the ratio of cells which appear red and which can grow on a non-fermentable carbon source. Suppressor mutations may be induced by test agents either on the mitochondrial genome or on the nuclear genome. Alternatively, epigenetic mechanisms may be responsible for phenotypic reversion.

Under some circumstances it may be desirable to confirm that the mutation is on the mitochondrial genome. One method for so doing is to mate or fuse the putative mitochondrial dysfunctioning cell with a cell which has no mitochondrial genome. Failure to change the mitochondrial phenotype upon mating or fusing suggests that the agent induced a mitochondrial mutation. The mitochondrial phenotype can be tested on either a non-fermentable medium or on a glucose medium and scored for failure to grow or red pigment accumulation, as discussed above.

Kits may be formulated for practicing the present invention. The kits may be for practicing the forward or backward direction of the bioassay. The kits will contain in one or more associated containers a sample of cells which are auxotrophic for adenine, medium containing a fermentable and medium containing a non-fermentable carbon source. Instructions for carrying out the invention may be contained as a package insert, or as a computer readable medium, or as a reference to a published paper or website. Preferably all components of the kit will be in a single container. Depending on whether the kit is for the forward or backward bioassay, the cells will contain functional or non-functional mitochondria.

The above disclosure generally describes the present invention. A more complete understanding can be obtained by reference to the following specific examples which are provided herein for purposes of illustration only, and are not intended to limit the scope of the invention.

EXAMPLE 1

This example demonstrates the effect of adriamycin on the generation of cells defective in mitochondrial function.

Figure 1A:
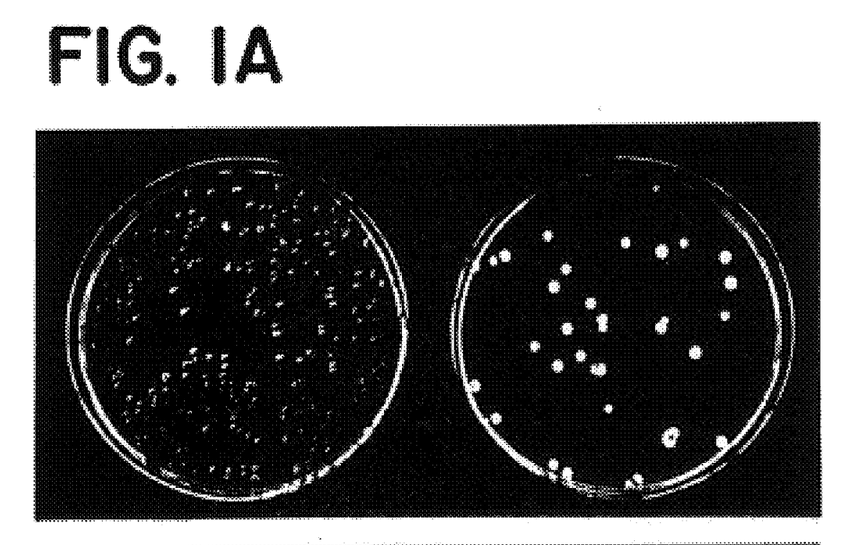
Figure 1B:
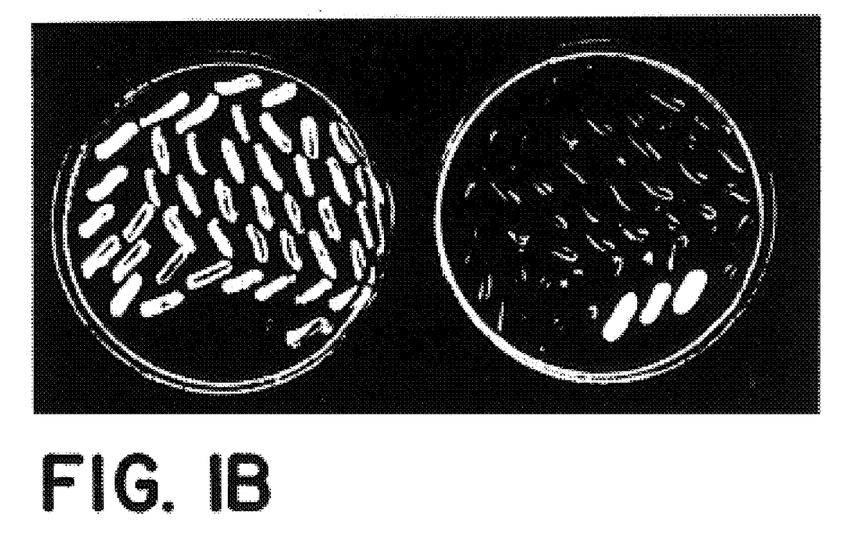
Figure 2:
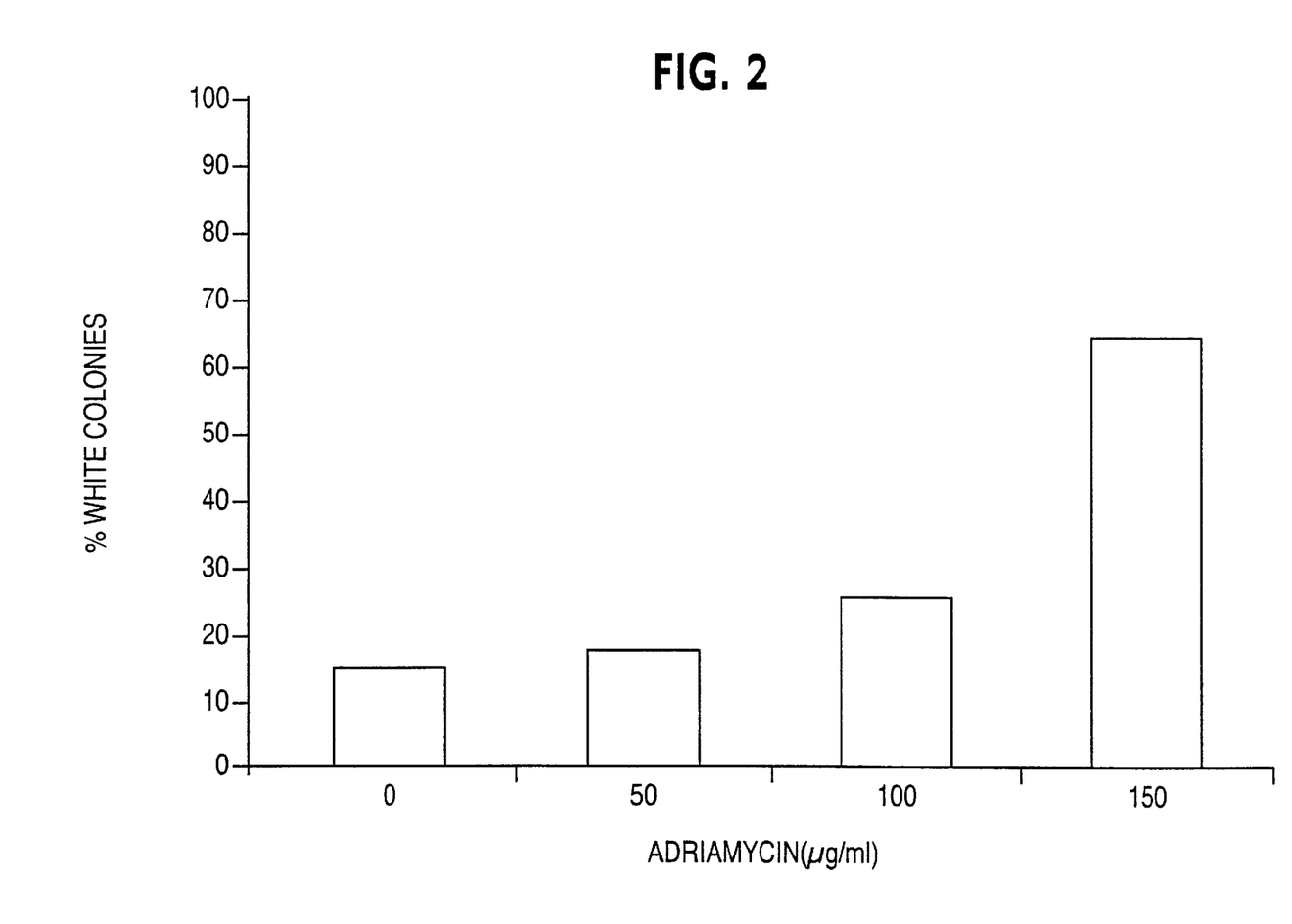

The yeast S. cerevisiae strain YPH499 (a ura3-52, lys2-801, ade2-101, trpl-63, his3-200, leul-1) was grown in YPD to log phase. Cell were then harvested and suspended in water containing various concentration of adriamycin for one hour. In order to test whether white colonies were defective in mitochondrial function, we transferred the colonies to an agar media containing glycerol (nonfermentable carbon source). Utilization of glycerol by an eukaryotic cell requires intact mitochondrial function (2). As shown in FIG. 1B, when randomly chosen white colonies were patched on glycerol plates, none were able to grow indicating a defect in mitochondrial function. As shown in FIG. 2, exposure of yeast cells resulted in increase number of white colonies with increasing dose of adriamycin. The number of surviving colonies that were white reached about 30% at 150 μg/ml concentration. These results indicate that mitochondrial dysfunction can be measured by red to white color change and that adriamycin induced mitochondrial dysfunction.

EXAMPLE 2

This example analyzes the nature of mitDNA in white cells after adriamycin treatment.

Figure 3A:
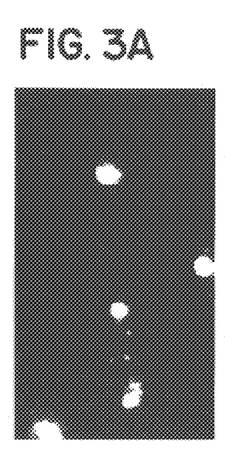
Figure 3B:
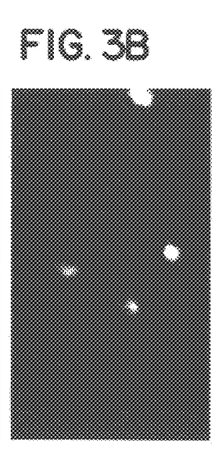
Figure 3C:
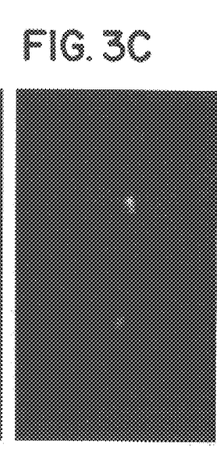
Figure 3D:
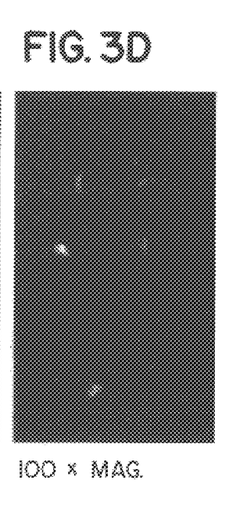

DNA was stained with a fluorescent dye, 4,6-diamidino-2-phenylindole (DAPI)(2). FIG. 3A demonstrates that both the nuclear and mitDNA were stained in wild type yeast cells. However, when several white colonies obtained after treatment with adriamycin were stained, it produced two types of DNA staining 1) colonies whose cells lost their mitDNA (FIG. 3C, only nuclear DNA is stained) and 2) colonies whose cells contained the mitDNA (FIG. 3D, both nuclear and mitDNA are stained). In this study, a known yeast strain lacking mitDNA (Rho$^0$) served as a negative control (FIG. 3B, only nuclear DNA is stained).

EXAMPLE 3

This example demonstrates that adriamycin directly effects mitDNA.

Figure 4A:
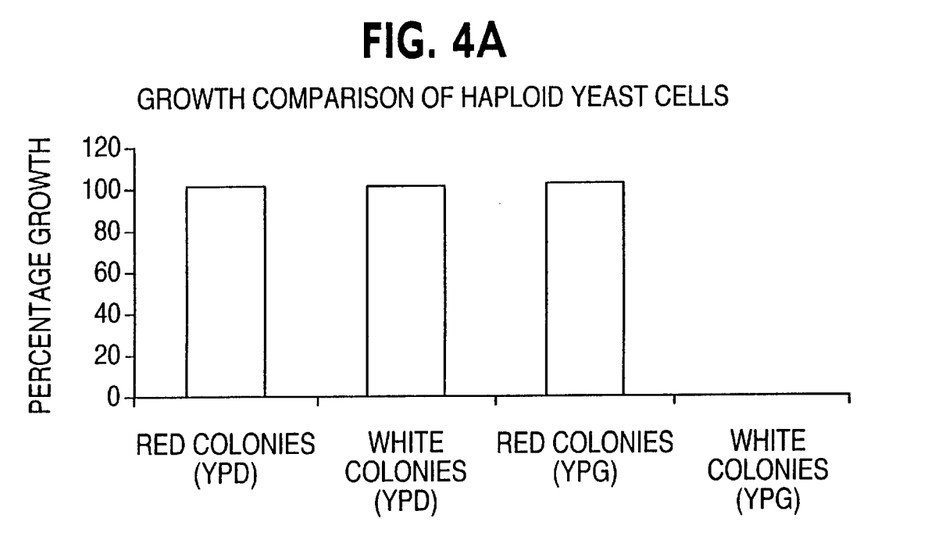
FIGS. 4A and 4B show growth comparison of haploid and diploid S. cerevisiae cells.
Figure 4B:
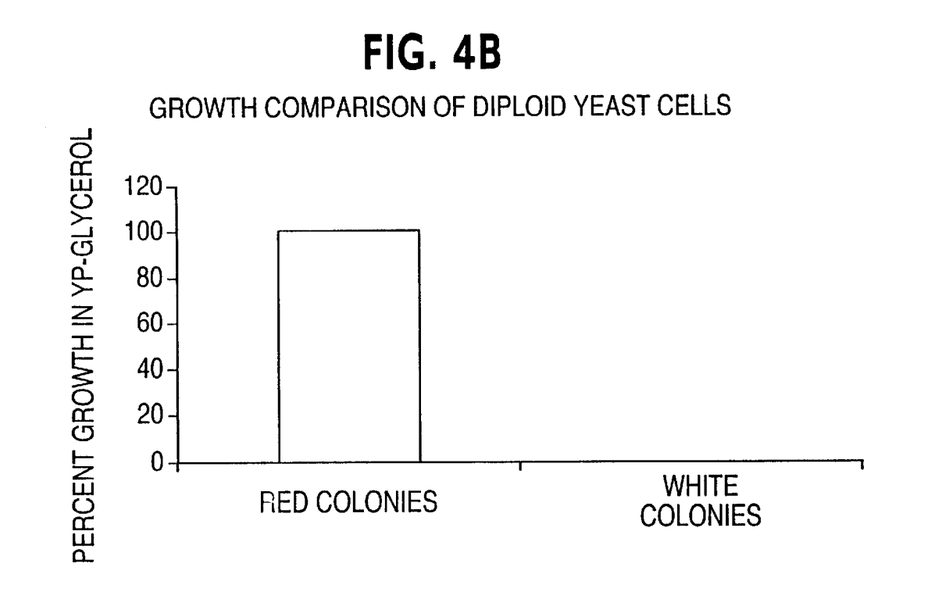

The genetic approach employed involved mating haploid white colonies generated after adriamycin treatment (shown in FIG. 2, "a" mating type) with a haploid Rho$^0$ strain (of opposite mating type "α" YPH 500 (ura3-52, lys2-801, ade2-101, trpl-63, his3-200, leu2-1) lacking mitDNA (3). The diploid cells (a total of 143) were tested for growth on glycerol medium. If the white cells contained a mutation in a nuclear gene affecting the mitochondrial function, it can be expected that diploid cells will grow on glycerol because a nuclear defect can be complemented with Rho$^0$ (because it contains intact nuclear DNA but lacks mitDNA). When diploid cells were tested in this manner, none grew on glycerol medium (FIG. 4). Together, these studies indicate that adriamycin preferentially damages mitDNA. This preferential damage by adriamycin can result either in complete loss of mitDNA (due to severe damage) and/or mutations in mitDNA (due to minor damage FIG. 3).

EXAMPLE 4

Figure 5A:
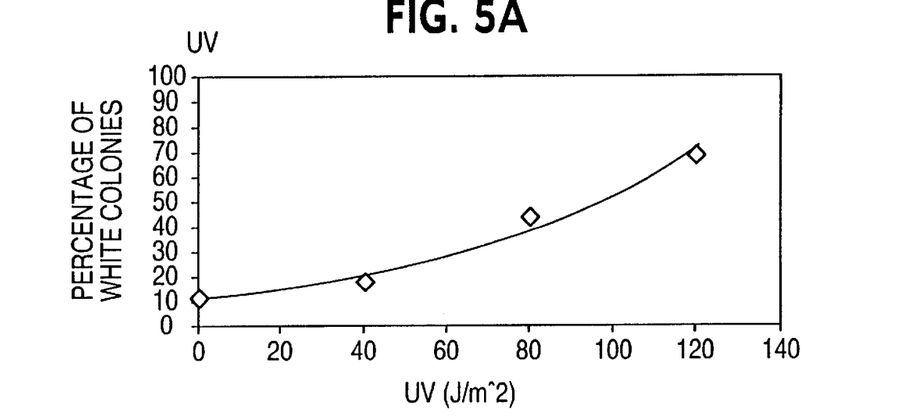
FIGS. 5A, 5B, and 5C show the percentage of white colonies produced after treatment with physical or chemical agents. Exponentially growing cells were treated with various doses of UV (FIG. 5A) or various lengths of time (MMS (FIG. 5B) and $H_2O_2$ (FIG. 5C)). For UV treatment appropriate dilutions of culture were plated on YPD agar and exposed to UV using STRATALINKER (Stratagene). For MMS and $H_2O_2$ treatments, cells were exposed in liquid YPD medium.
Figure 5B:
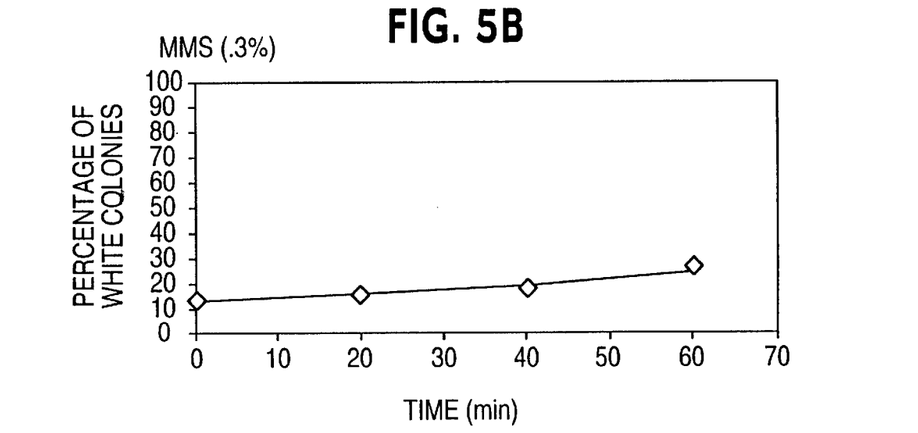
Figure 5C:
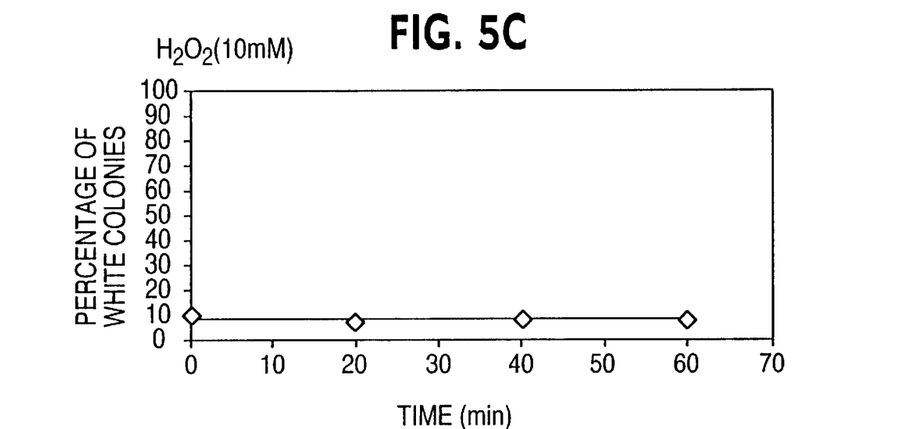
Figure 6A:
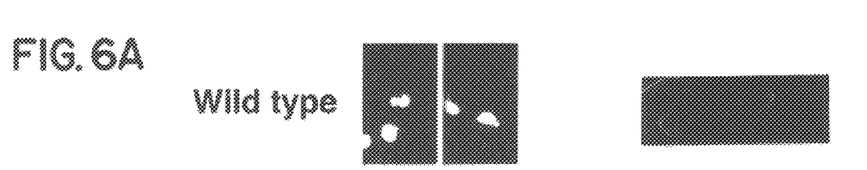
FIGS. 6A–F show that mitochondrial genome changes are induced by physical and chemical agents identified in the method. White S. cerevisiae colonies produced after treatment with physical or chemical agents were grown to log phase and stained with DAPI.
Figure 6B:
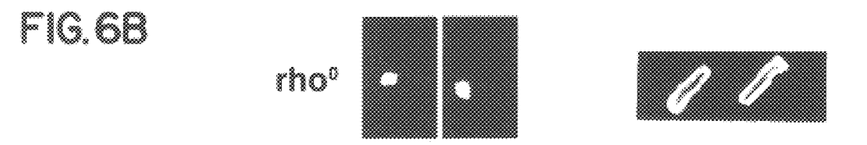
Figure 6C:
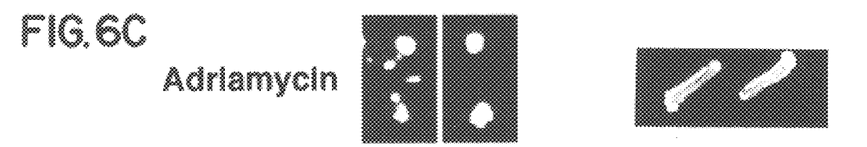
Figure 6D:
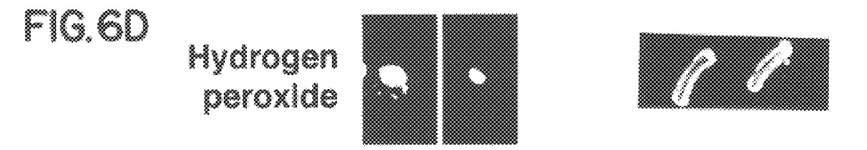
Figure 6E:
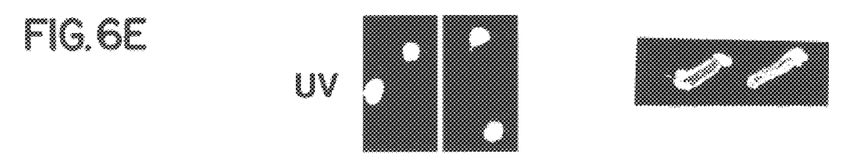
Figure 6F:
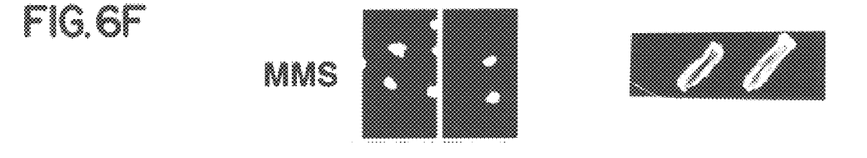

This example demonstrates that the colorimetric method can be used to measure mitochondrial dysfunction induced by physical environmental agents like ultra violet light (UV), and chemical agents like hydrogen peroxide ($H_2O_2$) and methyl methane sulphonate (MMS). FIG. 5 indicates that while $H_2O_2$ did not result in increased white colonies, UV and MMS did. These white colonies when tested do not grow on glycerol indicating a defect in mitochondrial function. The microscopic and genetic tests (as described above) revealed that white colonies either contained mutant mitDNA or lacked mitDNA at all (FIG. 6).

REFERENCES

1. Singh K K (1998) Mitochondrial DNA mutations in aging, disease and cancer. Springer, N.Y. pp1–15
2. Schatz G (1995) Biochim Biphys Acta 1271:123–126.
3. Tzagoloff A (1982) Mitochondria. New York, Plenum Press
4. Scheffler I (1999) Mitochondria, New York, Wiley-Liss.
5. Mihara K (2000) BioEssays 22:364–371.
6. Richter C (1988) FEBS Lett 241:467–473.
7. Shigenaga M K, Hagen T M, Ames B N (1994) Proc Natl Acad Sci U S A. 91:10771–8
8. Grossman L I and Shoubridge E A (1996) BioEssays 18:983–991.
9. Polyak K, Li Y, Zhu H, Lengauer C, Willson J K, Markowitz S D, Trush M A, Kinzler K W, Vogelstein B. (1998) Nat Genet.;20:291–3
10. Fliss M S, Usadel H, Caballero O L, Wu L, Buta M R, Eleff S M, Jen J, Sidransky D (2000) Science 287:2017–2019
11. Shofffier J M and Wallace D C (1992) Heart Disease Stroke 235–241.
12. Luft R (1994) Proc Natl Acad Sci 91:8731–8738.
13. Kang D, K. Takeshig, Sekiguchi M. and Singh K. K. (1998) An introduction. In Mitochondrial DNA mutations in Aging, Disease, and Cancer, Springer, New York. N.Y.
14. Rassmussen L and Singh K. K. (1998) Genetic integrity of mitochondrial genome. In Mitochondrial DNA mutations in Aging, Disease, and Cancer. Springer, New York. N.Y.
15. Wallace D C (1999) Science 283:1482–8.

What is claimed is:

1. A method for identifying agents which induce mitochondrial dysfunction, comprising:
   contacting eukaryotic cells which are auxotrophic for adenine with a test agent;
   culturing the eukaryotic cells on a medium comprising glucose;
   scoring fraction of the eukaryotic cells which appear white;
   testing the white eukaryotic cells to determine the ability to grow on a non-fermentable carbon source;
   identifying the test agent as a mitochondrial dysfunction inducer if the test agent increases the fraction of the eukaryotic cells which become white and which are unable to grow on the non-fermentable carbon source relative to control eukaryotic cells which have not been contacted with the test agent.

2. The method of claim 1 wherein the eukaryotic cells are yeast.

3. The method of claim 1 wherein the eukaryotic cells are *Saccharomyces cerevisiae*.

4. The method of claim 1 wherein the eukaryotic cells are ade1.

5. The method of claim 1 wherein the eukaryotic cells are ade2.

6. The method of claim 1 wherein the non-fermentable carbon source is glycerol.

7. A method for identifying agents which enhance mitochondrial function, comprising:
   contacting eukaryotic cells which are auxotrophic for adenine and defective in mitochondrial function with a test agent;
   culturing the eukaryotic cells on a medium comprising glucose;
   scoring fraction of the eukaryotic cells which appear red;
   testing the red eukaryotic cells to determine the ability to grow on a non-fermentable carbon source;
   identifying the test agent as a mitochondrial function enhancer if the test agent increases the fraction of the eukaryotic cells which become red and which are able to grow on the non-fermentable carbon source relative to control eukaryotic cells which have not been contacted with the test agent.

8. The method of claim 7 wherein the eukaryotic cells are yeast cells.

9. The method of claim 7 wherein the eukaryotic cells are *Saccharomyces cerevisiae*.

10. The method of claim 7 wherein the eukaryotic cells are ade1.

11. The method of claim 7 wherein the eukaryotic cells are ade2.

12. A kit comprising:
   a sample of eukaryotic cells which are auxotrophic for adenine;
   a non-fermentable medium for growth of the eukaryotic cells;

a fermentable cell medium for growth of the eukaryotic cells; and instructions for testing agents for the ability to affect mitochondrial function.

13. The kit of claim 12 wherein the eukaryotic cells have functional mitochondria.

14. The kit of claim 12 wherein the eukaryotic cells have dysfunctional mitochondria.

15. The kit of claim 12 wherein the cells are yeast cells.

16. The method of claim 2 wherein the yeast cells are haploid.

17. The method of claim 16 further comprising:

mating the haploid white yeast cells with a haploid yeast cell of opposite mating type which lacks a mitochondrial genome to form diploid cells;

testing the diploid cells for ability to grow on a nonfermentable carbon source, wherein inability to grow on a nonfermentable carbon source indicates that the test agent induces mitochondrial mutations.

18. The method of claim 16 further comprising:

mating the haploid white yeast cells with a haploid yeast cell of opposite mating type which lacks a mitochondrial genome to form diploid cells;

culturing the diploid cells on a medium comprising glucose and scoring red or white colony appearance, wherein a white appearance indicates that the agent induces mitochondrial mutations.

19. The method of claim 1 wherein the test agent is a known drug.

20. The method of claim 7 wherein the test agent is a known drug.

21. The method of claim 1 wherein the test agent is a chemical agent.

22. The method of claim 7 wherein the test agent is a chemical agent.

* * * * *

UNITED STATES PATENT AND TRADEMARK OFFICE
CERTIFICATE OF CORRECTION

PATENT NO. : 6,479,251 B1
DATED : November 12, 2002
INVENTOR(S) : Keshav K. Singh It is certified that error appears in the above-identified patent and that said Letters Patent is hereby corrected as shown below:

Title page,
Item [56], References Cited, OTHER PUBLICATIONS, in the 2$^{nd}$ line of the Philip S. Perlman and Henry R. Mahler citation, delete "19983" and replace with -- 1998 --.

Column 2,
Line 52, delete "wee" and replace with -- were --.

Column 4,
Line 60, delete "30%" and replace with -- 70% --.

Signed and Sealed this

Twentieth Day of May, 2003

JAMES E. ROGAN
*Director of the United States Patent and Trademark Office*